United States Patent [19]

Bennett

[11] Patent Number: Plant 5,458

[45] Date of Patent: May 7, 1985

[54] MINIATURE ROSE PLANT

[76] Inventor: Cecilia L. D. Bennett, 489 Minot Ave., Chula Vista, Calif. 92010

[21] Appl. No.: 344,539

[22] Filed: Feb. 1, 1982

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by its very unusal distinctive beauty. The rich creamy cupped petals edged in pink and the exquisite beauty when fully open, make it unique.

1 Drawing Figure

The present invention relates to a new and distinct variety of hardy, dwarf, bush plant of miniature class; the variety being primarily characterized a pink blend, similar in color to Mrs. Aaron Ward, a climbing hybrid tea introduced by A. Dickson in 1922.

The variety is further characterized by:

Its very distinctive coloring and form.

A blush which spreads gently over the bloom as it matures.

The plant is upright, well branched, spreading and well foliaged. The foliage is small, medium green, very serrated and edged in deep red. The bloom is similar in coloring to Mrs. Aaron Ward. A rich cream color with outer edges of petals tinged in a delicate shade of rose when grown in the Chula Vista area.

The plant ranges in size from 18 to 24 inches when grown in the ground, will stay smaller when grown in a container.

The present variety of miniature rose was originated by me at Tiny Petal's Nursery located at Chula Vista, Calif., under careful observation, and is a cross of "Little Darling" a floribunda as the seed parent and "Elfinesque" the pollen parent. "Little Darling" was introduced by Elmer Rose Co., 1956 U.S. Plant Pat. No. 1,581, and "Elfinesque" was hibridized by Morey and introduced in 1973.

Subsequent to origination of the variety I successfully reproduced it at Tiny Petal's Nursery located at aforesaid with reproductions coming true in all respects.

The color photographs illustrate the variety.

Referring now specifically to the new and distinct variety of miniature rose plant, the following is a detailed description thereof in outline; all major color plate identification being by reference to The British Colour Council Horticultural Colour Chart.

Type: Hardy; dwarf; spreading; upright; seedling; greenhouse; outdoors; cut flowers; garden decoration; potted plant.

Class: Miniature. Variety name: "CREAM PUFF"

Flowers borne: one to a stem, also 3–5 to a stem on sturdy canes.

Quantity of bloom: An abundance of bloom when grown inside and outside of the hothouse.

Bud:

*Peduncle.*—About 1" to 1½" sturdy; errect; slightly reddish; Hairs—minute.

*Before calyx breaks.*—Size — small. Form pointed with a very small foliated apendages on surface of the bud section. Color — medium green with a reddish tinge.

*As calyx breaks.*—Color — a rich creamy yellow with heavy overtones of porcelain rose 620 page 147 spreading over the upper portions of outer petals. Opens well in all weather conditions.

Bloom:

*Size when fully open.*—Bloom averages between 1½41 to 2" in diameter.

*Petalage.*—Semi double — averaging 20 to 25 petals, arranged regularly with occasional petaloids.

*Form.*—High centered circular form. Opens slowly, petals rarely reflex below the horizontal line. Open flower reveals a very beautiful set of stamens.

Petals: Thick; excellent substance, matt surface on inside and outside of petals.

*Shape.*—Outside petals, broad lanceolate with very minute tip, intermediate petals, rounded lanceolate with minute tip; inner petals — slightly elongated with a very minute tip; a few petaloids in the center.

Color: (newly opened flower from a plant grown at Chula Vista, Calif.):

*Outside petals.*—Outside surface — deep porcelain rose 620 page 147, with mimosa yellow, 602/2, page 143, at the base of petal.

*Outside petals.*—Upper surface — mimosa yellow 602/3 page 143, with outer edge of petals tinged with 620/3, page 147.

*Intermediate petals.*—Upper surface — mimosa yellow 602/3 page 143, faintly tinged on the outer edge with porcelain rose 620/3 page 147.

*Intermediate petals.*—Outer surface — mimosa yellow 602/3 page 143.

*Inside petals.*—Upper surface — mimosa yellow 602/3 page 143 faintly tinged with porcelain rose 620/3 page 147 on the outer edge of the petals.

*Inside petals.*—Outer surface — mimosa yellow 602/3 page 143.

Behavior: Opens well in all weather. Excellent form; color long lasting. As bloom matures the porcelain rose color gently spreads over the bloom giving it a blush effect. At the same time the outer side of the petals gradually turn white. Petals stay poised upward at all times and as evening falls the petals slowly close. The bloom is very beautiful at all stages, especially fully open, displaying the stamens. At times the mimosa yellow is not prominent, and is replaced by the blush effect, as shown in the photograph.

Reproductive organs:

*Stamens.*—Abundant, arranged evenly around the pistil in a sunburst effect.

*Filaments.*—Varying lengths, yellow.

*Anthers.*—Well formed: yellow.

*Pollen.*—A large amount.

*Pistils.*—Short, a fair amount.

*Styles.*—A fair amount, reddish.

*Ovaries.*—All enclosed in calyx.

*Hips.*—It does set hips.

*Sepals.*—Spear shaped, reddish.

*Seed.*—A few.

Foliage:

*Leaves.*—Compound of seven; usually a set of three and five directly below the bud. Medium size foliage; semi-glossy.

*Leaflets.*—Shape: broad, nearly oval; apex acute; base rounded; margin serrated.

*Color.*—Medium green; newer growth darker; reddish tinge on outer edge of leaflet.

Rachis: about $\frac{5}{8}''$ long; grooved; underside sparsely thorny otherwise smooth.

*Stipules.*—Medium length; narrow to medium width; narrow points with an upcurve.

Growth:

*Habit.*—Dwarf; bushy; spreading; much branched.

*Growth.*—Vigorous.

*Canes.*—Medium; sturdy.

*Main stems.*—Color: medium green.

*Thorns.*—Small to medium; hooked slightly downward; Color; reddish.

*Prickles.*—None.

*Branches.*—Color: medium green, slightly thorny; moderate number; branches sturdy.

The miniature rose plant and its flowers as herein described may vary in slight detail due to climatic, soil and cultural conditions under which the variety may be grown; the present description being of the variety as grown at Chula Vista, Calif.

I claim:

1. A new and distinct variety of miniature rose plant of hardy, dwarf, bushy, much branched habit, substantially as illustrated and described, characterized by bud and flowers similar in color to the variety, Mrs. Aaron Ward, a climbing hybrid tea: plant is easy to grow from cutting or bud.

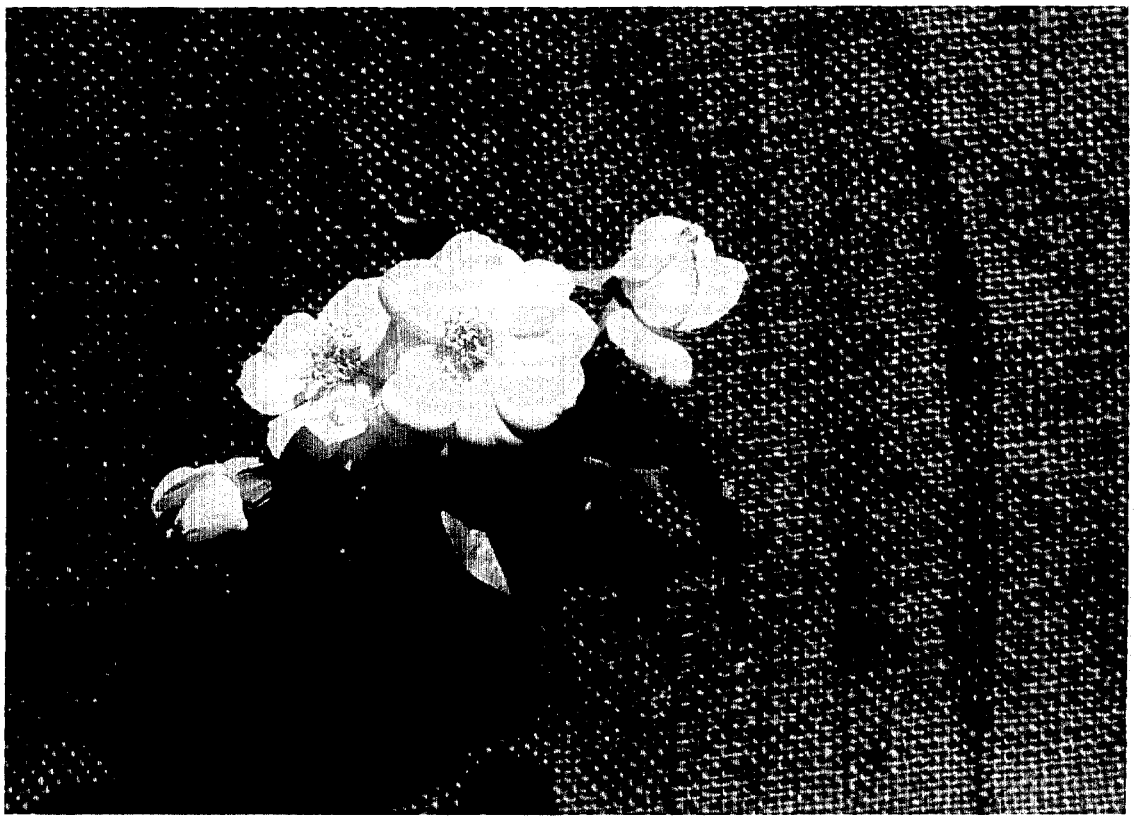

* * * * *